| United States Patent [19]
Grega et al.

[11] 3,941,783
[45] Mar. 2, 1976

[54] PROCESS FOR THE PRODUCTION OF N,N-DISUBSTITUTED CARBOXYLIC AMIDES

[75] Inventors: Erzsébet Grega; Pál Gribovszky; Sándor Marösvolgyi; Zoltán Pintér; Gyula Szilágyi; István Szita, all of Miskolc; Csaba Tarr, Sajobabony; László Tasi, Miskolc, all of Hungary

[73] Assignee: Eszakmagyarorszagi Vegyimuvek, Sajobabony, Hungary

[22] Filed: Dec. 4, 1973

[21] Appl. No.: 421,642

[52] U.S. Cl....... 260/247.7 V; 260/291; 260/558 R; 260/558 D; 260/558 P; 260/559 R; 260/561 R; 260/562 B; 260/562 P
[51] Int. Cl.²........................................ C07D 295/00

[58] Field of Search..... 260/247.7 H, 558 R, 558 D, 260/558 P, 561 R, 562 R, 559 R

[56] References Cited
OTHER PUBLICATIONS

Degering; E. R., An Outline of Organic Nitrogen Cmpds., Univ. Lithoprinters, Ypsilanti, Mich., 1950, p. 492.

*Primary Examiner*—Anton H. Sutto
*Assistant Examiner*—P. J. Killos
*Attorney, Agent, or Firm*—Young & Thompson

[57] ABSTRACT

A process for the production of N,N-disubstituted carboxylic amides by reacting carboxylic acid with carbamoyl chloride.

2 Claims, 4 Drawing Figures

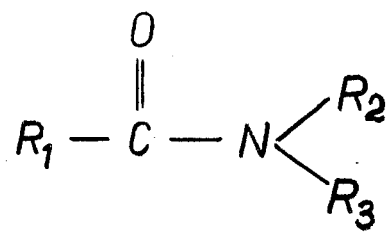
I.
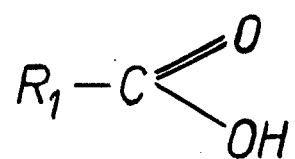
II.
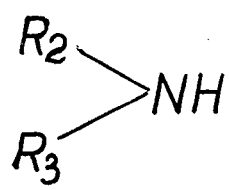
III.
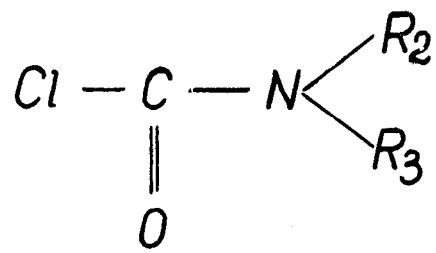
IV.

PROCESS FOR THE PRODUCTION OF N,N-DISUBSTITUTED CARBOXYLIC AMIDES

The present invention relates to a process for the production of N,N-disubstituted carboxylic amides of the general formula I

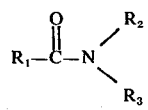

wherein $R_1$ is $C_2 - C_{18}$ straight or branched alkyl, a halogen-substituted alkyl, a phenyl-substituted alkyl, a phenyl, chloro- or dichloro-substituted phenyl, nitro- or dinitro-substituted phenyl, a trimethoxyphenyl, six-membered unsaturated heterocyclic radical having a nitrogen atom;

$R_2$ and $R_3$ are identical or different, $C_1 - C_4$ straight or branched alkyl, phenyl or $R_2$ and $R_3$ form together a six-membered heterocyclic radical having a nitrogen and an oxygen atom.

Compounds of the general formula I comprise a great number of important plant protecting agents and drugs. Plant protecting agents of this type are very advantageous selective weed killers. Some of the drugs are tranquillizers, others can be applied against arteriosclerosis while some are analeptic agents.

Compounds of the general formula I can be considered as N,N-disubstituted carboxylic amides but also as acylated amines.

Consequently there are two ways for the production of compounds of the general formula I: acylation of secondary amines or alkylation of carboxylic amines.

A great number of possibilities of the acylation of amines are described in the literature of organic chemistry (Houben-Weyl: Methoden der organischen Chemie, 8, 118 /1952/). Thus the acylation by carboxylic anhydrides or carboxylic esters is known when besides the acylated amine a carboxylic acid and alcohol, respectively, are formed. A draw-back of this method is that it can be applied only in case of amines of a low number of carbon atoms and primarily in case of primary amines. (A. Kaufmann: Ber. 42, 3480 /1909/; H. Honecka: J. Chem. Soc., 99, 428 /1911/).

Acylation with carboxylic chlorides can be carried out more favourably at a higher reaction rate. However this reaction is very exothermic and thus, in order to control the acylation process, the disposal of the liberated heat of reaction is indispensable. Also the formed hydrochloric acid must be bound because it may react with the initial amine and thus decreases the yield of the conversion. In addition to that the preparation and purification of the chlorides of carboxylic acids with longer chain is rather difficult (Ch. E. Gaspari: J. Amer. Chem. Soc., 27, 305 /1902/; W. Weaver, W. M. Whaley: J. Amer. Chem. Soc., 69, 1144 /1947/).

Also the acylation of amines with carboxylic acids can be carried out at high temperature, using primary amines and carboxylic acids with a short carbon chain when the formed water is removed in a continuous operation, e.g., by distillation as a xylene-containing azeotrop. This technique can be used, however, only in case of primary amines and of amines and carboxylic acids not sensitive to heat. The acylation of primary amines with carboxylic acids on using phosphorus trichloride is described by H. W. Grimmel: J. Amer. Chem. Soc., 68, 539 /1946/ and by other authors. In this case the amine forms with phosphorus trichloride an intermediate phosphorus aza compound which converts then into an amine acylated with the carboxylic acid.

Acylations with phosphorus oxychloride, phosphorus pentoxide, tetramethyl phosphite and carboxylic acid are also known. In these cases the reaction proceeds through the formation of phosphoric acid esters.

In the Hungarian Pat. No. 159044 the chloroacylation of secondary amines with the use of secondary amine, chlorocarboxylic acid and phosphorus trichloride is described.

Though from practical aspects a less significant method of producing acid amides by the hydrolysis of carboxylic nitriles is also known (C. Engler: Ann., 149 305 /1869/).

Another method described in literature for the production of N,N-disubstituted carboxylic amides is the alkylation of acid amides. In this case the carboxylic acid is converted with ammonia into carboxylic amide which latter is then treated with a known alkylating agent (such as an alkyl halide, dialkyl sulphate, potassium alkyl sulphate) (A. W. Titherley: J. Chem. Soc. 79, 393 /1901/). In certain cases the acid amide is first converted with sodium amide dissolved in an inert solvent into the sodium salt which latter is subjected to alkylation. By this method a monosubstituted acid amide is obtained in the first step. After converting this product into a sodium salt, the N,N-disubstituted acid amides are formed by alkylating these sodium salts.

Carbamoyl chlorides formed on treating cold primary amines with phosgene, obtained in general as intermediates in the production of isocyanates are dealt with extensively in literature. It is striking in turn that only a few papers are devoted to carbamoyl chlorides formed on treating secondary amines with phosgene and to the further reactions or these compounds.

It was reported by W. Price (J. Chem. Soc. 125, 115 /1924/) that the reaction with alcohols of carbamoyl chlorides formed with secondary amines leads to urethanes. Further, it is known that they give substituted ureas with amines (Houben-Weyl: 8, 118 /1952/). It is known as well that carbamoyl chlorides react with aromatic compounds under the conditions of the Friedel-Crafts reaction in the conventional solvents at 50° - 80 °C, affording carboxylic amides (Houben-Weyl: 8, 380 /1952/).

In the course of our experiments conducted on developing the present invention we have found that N,N-disubstituted carboxylic amides of the general formula I wherein $R_1$ is a $C_2 - C_{18}$ straight or branched alkyl, a halogen-substituted alkyl, a phenyl-substituted alkyl, a phenyl, chloro- or dichloro-substituted phenyl, nitro- or dinitro-substituted phenyl, a trimethoxyphenyl, a six-membered unsaturated heterocyclic having a nitrogen atom; $R_2$ and $R_3$ are identical or different, $C_1-C_4$ straight or branched alkyl, a phenyl, or $R_2$ and $R_3$ form together a six-membered heterocyclic having a nitrogen or an oxygen atom. The compounds can be produced practically in one single step in an essentially simpler way than the methods described in literature.

We have found that these N,N-disubstituted carboxylic amides can be produced when carboxylic acids of the general formula

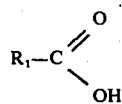

in which formula $R_1$ denotes the same radicals as specified above, are allowed to react at high temperature with carbamoyl chloride of the general formula

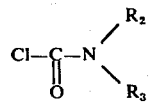

in which formula $R_2$ and $R_3$ have the same meaning as specified above. In this reaction carbon dioxide is formed as by-product, and the completion of the reaction is indicated by the end of gas evolution.

Carboxylic acid is reacted with carbamoyl chloride at 100°–300°C, preferably at 110°–220 °C. The process of the invention offers the advantage that pure N,N-disubstituted carboxylic amides can be produced in high yield in a single step from readily available and easily treatable starting materials. An extremely favourable feature is the possibility of producing a wide variety of disubstituted carboxylic amides by the process since the applied carboxylic acid may be a $C_2 - C_{18}$ alkyl carboxylic acid of straight or branched chain or it may be a halocarboxylic acid or an aryl or substituted aryl carboxylic acid and even a heterocycle as well. The range of secondary amines suitable for use is similarly very wide.

A particular advantage of the technique of the process applied without any solvents is that the gaseous products spontaneously separate from the disubstituted acid amide obtained in solid state and thus a separation procedure becomes superfluous.

The process according to the invention can be carried out batchwise though a further of its advantages is the possibility of a continuous operation in equipments conventionally used in the chemical industry. This continuous technique needs only a packed column, a film evaporator, a precipitator and a centrifuge.

The process according to the invention is illustrated by the following examples which, however, do not limit the field of protection of the patent.

EXAMPLE 1

To a 250 ml. flask equipped with gas outlet pipe, 25.6 g. of palmitic acid and 19.1 g. of N,N-dibutylcarbamoyl chloride are added. The reaction mixture is heated at a steady rate to 130 °C within about 30 minutes when gas evolution starts. The mixture is kept at a temperature of 130°–160°C for an hour when the gas evolution terminates. On pouring the melt in 100 ml. of cold water, the melt is extracted with 100 ml. of benzene, the extract dehydrated on sodium sulphate and benzene distilled off in vacuo. The residual yellowish oil converts into white crystals on cooling. Yield: 27.2 g. (74.8%) of N,N-dibutylpalmitic amide, m.p.: 37°C.

Analysis: Calculated: N 3,83 %; Found: N 3.77 %.

EXAMPLE 2

To a 250 ml. flask equipped with a gas outlet pipe, 3.5 g. of benzoic acid and 5.0 g. of N-isopropyl-N-phenyl-carbamoyl chloride are added, then the mixture heated up to 140°C in about half an hour, when gas evolution started. The reaction mixture is kept for about an hour at 140°–170°C, then the gas evolution ceased. The melt is poured on 150 ml. of water under stirring. The precipitated crystals are filtered through a sintered glass filter, washed with 2 × 20 ml. of water and dried. Yield: 5.7 g. (78 %) of N-ispropyl-N-phenyl benzoic amide, m.p.: 55°–56 °C.

Analysis: Calculated: N 5.86 %; Found: N 5.98 %.

EXAMPLE 3

To a flask as specified in Example 1, 9.88 g. of N-isopropyl-N-phenyl-carbamoyl chloride and 5.02 g. of monochloroacetic acid are added. The reaction mixture is heated to a temperature of 120°C and stirred for an hour at this temperature until the gas evolution is ended. Then the melt is poured in 100 ml. of water. The precipitated crystals are filtered, washed with 2 × 20 ml. of water and dried. Yield: 9.6 g. (90.7 %) of N-isopropyl-N-phenyl-chloroacetamide, m.p.: 76.5°C.

Analysis: Calculated: Cl: 16.74%; N 6.61%; Found: Cl: 16.97%; N 6.87%.

EXAMPLE 4

To a 250 ml. flask equipped as specified in Example 1, 9.58 g. of N,N-dibutyl carbamoyl chloride and 10.6 g. of 3,5-dinitrobenzoic acid are added, and the mixture heated to a temperature of 140° – 160°C when the gas evolution starts. The mixture is kept at this temperature for about 90 minutes until the gas evolution is ended. Then, on cooling, the mixture is poured into 100 ml. of water under stirring, and extracted with 100 ml. of benzene. The organic phase separated from the aqueous phase is dried on sodium sulphate then the benzene distilled off. The residue solidifies in a short time on standing. Yield: 12 g. (74 %) of N,N-dibutyl-3,5-dinitrobenzoic amide, m.p.: 61°–62 °C.

Analysis: Calculated N 13.0%; Found N 12.71%.

EXAMPLE 5

To a 500 ml. flask equipped as specified in Example 1, 16.0 g. of morpholino-carbamoyl chloride and 22.5 g. of 3,4,5-trimethoxybenzoic acid are added. The mixture is heated to 120° – 140°C and kept for 90 minutes at this temperature. After the termination of gas evolution, 100 ml. of water is added, the mixture boiled for 10 to 15 minutes under a reflux condenser, then filtered through a folded filter and the filtrate cooled to below 5°C. The precipitated crystals are filtered through a sintered glass filter and dried. Yield: 23.0 g. (82%) of N-(3,4,5-trimethoxybenzoyl)-tetrahydro-1,4-oxazine, m.p.: 116°C.

Analysis: Calculated: N 4.98 %; Found: N 4.94 %.

EXAMPLE 6

To a 250 ml. flask equipped as specified in Example 1, 4.62 g. of N,N-diphenylcarbamoyl chloride and 2.3 g. of monochloroacetic acid are added, then the mixture heated to 120° – 130°C and kept at this temperature until the gas evolution stops, for about an hour. Then the melt is poured in 50 ml. of water. The precipitated crystalline substance is filtered, washed with 2 × 10 ml. of water and dried. Yield: 4.65 g. (94.7%) of N,N-diphenylchloroacetic amide, m.p.: 115° – 118°C.

Analysis: Calculated: Cl 14.42 %; N 5.71 %; Found: Cl 14.63%; N 5.68 %.

EXAMPLE 7

To a 500 ml. flask equipped as specified in Example 1, 19.8 g. of N-isopropyl-N-phenylcarbamoyl chloride and 25.6 g. of palmitic acid are added. On heating the mixture to a temperature of 140°C it is kept for 90 minutes at 140° – 180°C. After the termination of gas evolution, the mixture is cooled to a temperature of 20°C, 20 ml. of ether added and the precipitated crystals of the amine salt separated by filtering. The ethereal solution is evaporated in vacuo, the residue poured in 50 ml. of ice water, filtered and dried. Yield: 31 g. (84 %) of N-isopropyl-N-phenylpalmitic amide, m.p.: 31°C.

Analysis: Calculated: N 3.75 %; Found: N 3.68 %.

EXAMPLE 8

To a 350 ml. flask equipped as specified in Example 1, 19.1 g. of N,N-dibutylcarbamoyl chloride and 12.2 g. of benzoic acid are added. On heating the mixture to 110°C the gas evolution starts and is continued for about 90 minutes at a temperature of 110° – 130°C. Then the reaction mixture is poured in 100 ml. of water and extracted with 100 ml. of benzene. The benzene phase is separated from the aqueous phase, dried with sodium sulphate, then the solvent distilled off. The product is separated in vacuo by fractionated distillation. Yield: 18.0 g. (77.5%) of N,N-dibutyl-benzoic amide, a colourless oil, b.p.: 144°C at 14 torr.

Analysis: Calculated: N 6.0 %; Found: N 5.95%.

EXAMPLE 9

To a 350 ml. flask equipped as specified in Example 1, 15 g. of morpholinocarbamoyl chloride and 12.5 g. of benzoic acid are added, and the mixture heated to 150° – 160°C where the gas evolution continues for half an hour. The melt is poured in 50 ml. of water and extracted with 50 ml. of benzene. On separating the organic phase it is dried with sodium sulphate, and subsequently separated by fractionated vacuum distillation. Yield: 17 g. (89%) of N-benzoyl-tetrahydro-1,4-oxazine, a colourless oil of b.p. 178°–182°C at 13 torr.

Analysis: Calculated N 8.5 %; Found: N 8.5 %.

EXAMPLE 10

To a 500 ml. flask equipped as specified in Example 1, 24.6 g. of nicotinic acid and 28.5 g. of N,N-diethylcarbamoyl chloride are added. The mixture is heated up to a temperature of 190°–220°C and kept at this temperature for about 20–30 minutes until the gas evolution stops. The brown melt is separated by vacuum distillation. The distillate which boils at 155°–160°C at 10 torr consisting of 31.0 g. of nicotinic diethylamine is collected. Yield: 87.5 %.

Analysis: Calculated: N 15.7 %; Found: N 15.3 %.

EXAMPLE 11

To a 100 ml. flask equipped as specified in Example 1, 1.25 g. of diphenylacetic acid and 1.0 g. of dimethylcarbamoyl chloride are added, then the mixture heated to 120° – 140°C and kept at this temperature for half an hour. The melt is cooled to 80°C and poured in 20 ml. of water. The precipitated crystals are filtered, washed with small amounts of water and dried. Yield: 1.4 g. (100%) of 1,1-diphenyl-N,N-dimethylacetamide, m.p.: 128°–129°C.

Analysis: Calculated: N 5.85%; Found: N 5.96%.

EXAMPLE 12

To the equipment specified in Example 1, 31.3 g. of 2-chlorobenzoic acid and 27.1 g. of diethyl carbamoyl chloride are added, then the mixture heated to 130°–140°C and kept at this temperature for 45 minutes. The mixture is cooled and poured on 200 ml. of water, subsequently extracted with 100 ml. of benzene. The benzene phase is separated, dried over sodium sulphate and benzene removed by vacuum distillation. Yield: 38 g. (90.5%) of 2-chlorobenzoic diethylamide, a yellowish brown oil.

Analysis: Calculated Cl 16.8 %; N 6.65 %; Found: Cl 16.21%; N 6.41 %.

EXAMPLE 13

To the equipment specified in Example 1, 31.3 g. of 4-chlorobenzoic acid and 27.1 g. of diethylcarbamoyl chloride are added, then the mixture heated on an oil bath and kept for 30 minutes at 140° – 160°C. On cooling, the mixture is poured on water (of about 200 ml.) then extracted with 100 ml. of petroleum ether. Subsequently, petroleum ether is removed from the extract by vacuum distillation. Yield: 32 g. (76.5%) of 4-chlorobenzoic diethylamide, a yellow oil.

Analysis: Calculated: Cl 16.8 %; N 6.65 %; Found: Cl 16.6 %; N 6.35 %.

EXAMPLE 14

To the equipment specified in Example 1, 19.1 g. of 3,4-dichlorobenzoic acid and 13.5 g. of diethylcarbamoyl chloride are added. The mixture is heated on an oil bath to 140° – 160°C and kept at this temperature for 30 minutes. On cooling, the mixture is poured on 100 ml. of water and extracted with 50 ml. of petroleum ether. The extract is dried and the solvent removed. Yield: 22 g. (89.5%) of 3,4-dichlorobenzoic diethylamide, an orange-red oil.

Analysis: Calculated: Cl 28.8%; N 5.70 %; Found: Cl 28.4%; N 5.41 %.

EXAMPLE 15

To the equipment specified in Example 1, 19.1 g. of 3,4-dichlorobenzoic acid and 19.1 g. of diisobutylcarbamoyl chloride are added. On heating the mixture to 140°C it was kept for 30 minutes at 160° – 180°C. On cooling, the melt is poured on 100 ml. of water. The precipitated crystals are filtered through a sintered glass filter, washed with 2 × 20 ml. of water and dried. On recrystallizing the crude product from petroleum ether, yield: 25 g. (83.5%) of 3,4-dichlorobenzoic diisobutylamide, m.p.: 74°–76°C.

Analysis: Calculated: Cl 23.6%; N 4.68%; Found: Cl 24.07%; N 4.78%.

EXAMPLE 16

To the equipment specified in Example 1, 15.5 g. of 2-chlorobenzoic acid and 19.1 g. of diisobutyl carbamoyl chloride are added. The mixture is melted and kept for 30 minutes at 140° – 160°C. On cooling, it is poured on 100 ml. of water and extracted with 50 ml. of petroleum ether. The petroleum ether phase is dried, then the solvent removed by vacuum distillation. Yield: 22.5 g. (85.5%) of 2-chlorobenzoic diisobutylamide, a red oil.

Analysis: Calculated: Cl 13.35%; N 5.30 %; Found: Cl 12.94%; N 5.41%

EXAMPLE 17

To the equipment specified in Example 1, 19.1 g. of 3,4-dichlorobenzoic acid and 19.1 g. of di-sec-butylcarbamoyl chloride are added. The mixture is heated to 120°C and subsequently kept for half an hour at 120°–130°C until the gas evolution stops. Then the mixture is poured onto about 100 ml. of water. The precipitated 3,4-dichlorobenzoic di-sec-butylamide is filtered through a sintered glass filter, washed with 2 × 20 ml of water and dried. Yield: 24 g. (80%) of a substance with m.p.: 176°–180°C.

Analysis: Calculated: Cl 23.6 %; N 4.68 %; Found: Cl 24.07 %; N 4.45 %.

EXAMPLE 18

To a flask equipped as specified in Example 1, 25.6 g N-(2-methyl-6-ethyl)-phenyl-N-ethyloxymethyl-carbamoyl chloride and 10 g monochloro-acetic acid are added; the mixture is heated to a temperature of 120° – 140°C and kept at this temperature for 30 minutes until the gas evolution stops. The mixture is poured into 50 ml of water and taken up by 50 ml of benzene. After separating the benzene layer the solvent is distilled. 22 g N-(2-methyl-6-ethyl)-phenyl-N-ethoxy-methyl-chloracetamide is formed as a yellowish brown oil. Yield 82 %.

Analysis: Calculated: Cl 13.3 %; N 5.2 %; Found: Cl 12.97 %; N 5.03 %.

EXAMPLE 19

To a flask equipped as specified in Example 1, 29.8 g N-(2,6-diethyl)-phenyl-N-butoxymethyl-carbamoyl chloride and 10 g monochloro-acetic acid are added; the mixture is heated to a temperature of 120° – 140°C and kept at this temperature for 30–40 minutes until the gas evolution stops. Separated as in Example 27 25, g N-(2,6-diethyl)-phenyl-N-butoxy-methyl-chloroacetamido was obtained as a brownish oil. Yield: 80.5 %.

Analysis: Calculated: Cl 11.4 % N 4.51 % Found: Cl 10.9 % N 4.39 %

What we claim is:

1. Process for the production of N,N-disubstituted carboxylic amides of the formula

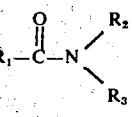

wherein
$R_1$ is $C_2 - C_{18}$ straight or branched alkyl, a halogen-substituted alkyl, a phenyl-substituted alkyl, phenyl, chloro- dichloro-substituted phenyl, nitro- dinitro-substituted phenyl, trimethoxyphenyl, six-membered unsaturated heterocyclic having a nitrogen atom;

$R_2$ and $R_3$ are identical or different, $C_1 - c_4$ straight or branched alkyl, phenyl or $R_2$ and $R_3$ form together a six-membered heterocycle with a nitrogen atom and an oxygen atom, characterized by reacting a carboxylic acid of the formula

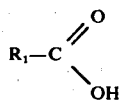

wherein $R_1$ has the same meaning as above, with a carbamoyl chloride of the formula

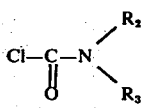

wherein $R_2$ and $R_3$ have the same meaning as above, at a temperature of 100° – 300°C., and separating the thus-formed N,N-disubstituted carboxylic amide from the reaction mixture.

2. A process as claimed in claim 1, in which said temperature is 110°–220°C.

* * * * *